United States Patent
Cook

[11] Patent Number: 6,072,079
[45] Date of Patent: Jun. 6, 2000

[54] CONTINUOUS PROCESS FOR THE PRODUCTION OF DIACETOXYBUTENE

[75] Inventor: Steven Leroy Cook, Kingsport, Tenn.

[73] Assignee: Eastman Chemical Company, Kingsport, Tenn.

[21] Appl. No.: 09/261,895

[22] Filed: Mar. 3, 1999

[51] Int. Cl.[7] .................................................. C07C 67/02
[52] U.S. Cl. ........................................ 560/261; 560/245
[58] Field of Search ..................................... 560/261, 245

[56] References Cited

U.S. PATENT DOCUMENTS

| | | |
|---|---|---|
| 5,189,199 | 2/1993 | Godleski . |
| 5,623,086 | 4/1997 | Perri et al. . |
| 5,663,422 | 9/1997 | Perri et al. . |

FOREIGN PATENT DOCUMENTS

| | | |
|---|---|---|
| 0 872 472 A1 | 10/1998 | European Pat. Off. . |
| 3245843 | 11/1991 | Japan . |
| 10114706 | 5/1998 | Japan . |

OTHER PUBLICATIONS

Shvets, V. F. et al, Kinet. Katal., 16(3) 785–788 (1975).
Shvets, V. F. et al, Kinet. Katal., 16(2) 425–430 (1975).
Swindell, C. S. et al, J. Org. Chem., 1990, 55, 3–5 (1990).
Fraser–Reid, B. and Rahman, Md. A., J. Amer. Chem. Soc., 107, No. 19, 5576–78 (1985).
Evans, R. M., et al., J. Chem. Soc. 248–258 (1949).

*Primary Examiner*—Paul J. Killos
*Attorney, Agent, or Firm*—Michael J. Blake; Harry J. Gwinnell

[57] ABSTRACT

Disclosed is a continuous process for the production of 3,4-diacetoxy-1-butene (DAcB) by the reaction of 3,4-epoxy-1-butene (EpB) with acetic anhydride ($Ac_2O$) in the presence of potassium acetate (KOAc) wherein the KOAc is formed in situ by contacting EpB, acetic anhydride and a potassium salt selected from potassium carbonate, potassium bicarbonate, potassium hydroxide or a mixture of any two or more thereof at elevated temperatures.

10 Claims, No Drawings

CONTINUOUS PROCESS FOR THE PRODUCTION OF DIACETOXYBUTENE

This invention pertains to a continuous process for the production of 3,4-diacetoxy-1-butene (DAcB) by the reaction of 3,4-epoxy-1-butene (EpB) with acetic anhydride ($Ac_2O$) in the presence of a potassium salt catalyst. More particularly, this invention pertains to the manufacture of DAcB by the esterification of EpB with $Ac_2O$ in the presence of potassium acetate (KOAc) wherein the KOAc is formed in situ by contacting EpB, acetic anhydride and a potassium compound selected from potassium carbonate, potassium bicarbonate, potassium hydroxide or a mixture of any two or more thereof at elevated temperatures.

Diacetate diesters may be prepared by acetylation of epoxides with $Ac_2O$ in the presence of various amine catalysts. See, for example, the processes described by Shevets, V. G. and A-Wahib, I., *Kinet. Katal.*, 16(3) 785–8 (1975); Shevets, V. G. and A-Wahib, I., *Kinet. Katal.*, 16(2) 425–30 (1975); Swindell, C. S. and Patel, B. P., *J. Org. Chem.* 55, 3 (1990); and Fraser-Reid, B. and Rahman, Md. A., *J. Amer. Chem. Soc.*, 107, 5576 (1985). In the studies by Shevets et al., 1,2-diacetoxyethane was synthesized from ethylene oxide and $Ac_2O$ using a pyridine catalyst and an N-(β-acetoxyethyl)pyridinium acetate intermediate was found to be involved in the transformation. The yields ranged from 45–93.5% and decreased with increasing pyridine (0.5–1.0 M). A similar reaction in the presence of a tetraethylammonium halide catalyst also gives the 1,2-diacetoxyethane. Swindell et al. discloses that acetic anhydride reacts with epoxycyclooctane in the presence of 1,8-diazabicyclo-[5.4.0]undec-7-ene (DBU) and LiCl in tetrahydrofuran (THF) to give the vicinal diacetate in 70% yield. Studies by Fraser-Reid et al. disclose the ring opening of epoxypyranosides with $Ac_2O$ catalyzed by tetrabutylammonium acetate to give the corresponding vicinal diacetates.

The acid-catalyzed ring opening of epoxides in the presence of $Ac_2O$ is well known. Evans, R. M., Fraser, J. B. and Owen, L. N., *J. Chem. Soc.*, 248 (1949) disclose that 3,4-epoxy-1-butene is converted to 3,4-diacetoxy-1-butene in 70% yield when hydrochloric acid is used as a catalyst, while only a 39% yield is obtained when anhydrous zinc chloride catalyst is used. Lewis acid catalysts do not give good process economic on commercial scale because of catalyst cost and the need to use expensive, corrosion-resistant materials of construction. S. A. Godleski discloses in U.S. Pat. No. 5,189,199 (1993) that the reaction of 3,4-epoxy-1-butene with acetic anhydride in the presence of a ligated Pd(0) catalyst gives a mixture of 1,4-diacetoxy-2-butene and 3,4-diacetoxy-1-butene.

Japanese Patent 03245843 A2 911101 Heisei, Chem. Abst. 116:105641 discloses that diacetoxylation of butadiene with acetic acid and oxygen produces either 1,4-diacetoxy-2-butene or 3,4-diacetoxy-1-butene. While limited to conjugated olefins, this process does provide an alternative route to these molecules. The catalyst typically consists of Sb-Pd-V on a $TiO_2$ support. A mixture of acetic acid, butadiene, and air is passed through a reactor containing the catalyst at 180° C. to give diacetoxybutene.

Perri, S. T. and Falling, S. N., U.S. Pat. No. 5,623,086 (1995), disclose the use of tetraalkylammonium acetates as catalysts for the conversion of EpB and $Ac_2O$ to DAcB. They also disclose, in U.S. Pat. No. 5,663,422 (1997), the preparation of DacB by the reaction of EpB with $Ac_2O$ in the presence of the much more thermally-stable tetraalkylphosphonium acetates. The phosphonium-based catalysts require a 2:1 $Ac_2O$:EpB mole ratio to give high selectivity to DAcB.

The manufacture of DacB by contacting EpB and $Ac_2O$ in the presence of the catalyst of choice, tetrabutylphosphonium acetate, has the disadvantage of being costly due, primarily, to the inability or difficulty in recoverying the expensive phosphonium catalyst from the process residue at the conclusion of the continuous manufacturing process. During the production and/or recovery/purification of DacB, high boiling materials (tars) form and accumulate with the phosphonium catalyst as process/distillation residue. All or a portion of these tars must be removed from the manufacturing process and, consequently, all of the expensive phosphonium catalyst cannot be recycled to the esterification process. Furthermore, the process used to prepare tetrabutylphosphonium acetate apparently utilizes a chloride compound resulting in the presence of residual chloride in the catalyst. This residual chlorine produces severe corrosion of the 304 stainless steel reactors. Some of the corrosion may be attributed to the corrosive acetic acid/acetic anhydride compositions, but chloride-promoted corrosion always is of concern in any stainless equipment.

A process has now been discovered in which DAcB is produced by contacting EpB and $Ac_2O$ in the presence of KOAc catalyst wherein the KOAc is formed in situ by contacting EpB, acetic anhydride and a potassium compound selected from potassium carbonate, potassium bicarbonate, potassium hydroxide or a mixture of any two or more thereof at elevated temperatures. The present invention therefore provides a process for the production of DAcB by the steps of (1) feeding EpB and $Ac_2O$ to a reaction zone while maintaining a concentration of KOAc of about 0.5 to 5.0 weight percent, based on the total weight of the materials present in the reaction zone, e.g., EpB, $Ac_2O$, DAcB and KOAc, and (2) removing crude product comprising DAcB from the reaction zone, wherein the KOAc initially is formed in situ by contacting EpB, $Ac_2O$ and a potassium compound selected from potassium carbonate, potassium bicarbonate, potassium hydroxide or a mixture of any two or more thereof and the reaction zone is maintained at a temperature in the range of about 100 to 140° C. When KOAc, rather than potssium carbonate, bicarbonate, and/or hydroxide is fed initially to the process, the initial reaction rate is very slow due primarily to the low solubility of KOAc in the initial reaction mixture. Although faster initial rates might be achieved at higher temperatures, the refluxing EpB (b.p.=66° C.) keeps the initial reaction temperature low at the outset unless pressurized equipment is used. I have discovered that if the reaction is continued long enough to obtain lower EpB concentrations and, consequently, higher temperatures, complete dissolution of the catalyst occurs. Thereafter, reaction rate increases smoothly. For batch operations, this effect would not be particularly useful because of the induction period. However, in a continuous process, e.g., continuous operation extending over a period of several days up to several months, steady-state conditions can be maintained in the range required for dissolution of the catalyst and acceptable rates of reaction can be achieved. Potassium carbonate appears to accelerate initial reaction of EpB to DAcB prior to complete dissolution and conversion to KOAc.

The temperature at which the process is carried out ranges from a low of about 80° C. at the start-up of the process up to about 140° C. when all, or substantially all, of the potassium carbonate, bicarbonate and/or hydroxide catalyst has been converted to dissolved KOAc catalyst. After the initial start-up period and during continuous operation, the reaction zone is maintained at a temperature in the range of about 100 to 140° C., preferably about 120 to 140° C.

Although the process may be operated at pressures moderately above or below atmospheric pressure, it is an advantage of the present invention that the process can be operated at ambient pressure without the need for costly pressure equipment.

The $Ac_2O$ and EpB may be added continuously or intermittently, separately or together, in amounts which give an $Ac_2O$:EpB mole ratio greater than 1, preferably mole ratios in the range of about 1.1:1 to 2:1. The amount of excess $Ac_2O$ usually is minimized to reduce the amount that must be recycled. The amount of potassium carbonate, bicarbonate and/or hydroxide initially charged to the reaction zone is at least 0.5 weight percent based on the total weight of the $Ac_2O$ and EpB employed initially. The potassium compound initially charged to the reaction preferably is potassium carbonate. The potassium carbonate, bicarbonate and/or hydroxide may be provided to the process as a solid in a finely divided form, e.g., as a powder or granulation. Alternatively, the potassium carbonate, bicarbonate and/or hydroxide may be fed as a solution in water or acetic acid. However, the presence of large amounts of acetic acid in the reaction zone mixture can result in the formation of significant amounts of monoester, i.e., 3,4-dihydroxy-1-butene mono-acetate. Therefore, the amount of acetic acid present in the reaction zone normally should be maintained at an amount which gives an acetic acid:$Ac_2O$ mole ratio of less than about 1:1. During most of the process when the reaction mixture of the reaction zone is homogeneous, i.e., when the catalyst is dissolved, the concentration of dissolved KOAc in the reaction mixture is maintained in the range of about 0.5 to 5.0 weight percent, preferably about 0.5 to 2.0 weight percent, based on the total weight of the reaction mixture. The dissolved KOAc may be replenished as necessary by feeding potassium carbonate, bicarbonate, hydroxide and/or acetate to the reaction zone.

Crude product comprising DAcB is removed intermittently or continuously from the reaction zone and fed to a purification zone where it is purified, e.g., by distillation to remove any catalyst residues, unreacted $Ac_2O$ or EpB or high-boiling materials present. The continuous process provided by the present invention preferably is operated in a manner which gives an $Ac_2O$ conversion of up to about 80% to avoid the formation of tars.

Alternatively, the process provided by the present invention may be defined as a process for the production of DAcB by the steps of (1) providing a reaction zone containing a reaction mixture comprising EpB, $Ac_2O$, at least about 50 weight percent, preferably about 50 to 70 weight percent, DAcB and about 0.5 to 5.0 weight percent, preferably about 0.5 to 2.0 weight percent, of dissolved KOAc and having a boiling point of about 100 to 140° C., preferably about 120 to 140° C.; (2) feeding EpB and $Ac_2O$ to the reaction mixture of step while maintaining the temperature of the mixture at about 100 to 140° C., preferably about 120 to 140° C., and while maintaining a concentration of KOAc of about 0.5 to 5.0 weight percent, based on the total weight of the materials present in the reaction mixture, e.g., EpB, $Ac_2O$, DAcB and KOAc;and (3) removing crude product comprising DAcB from the reaction zone.

EXAMPLES

The process provided by the present invention is further illustrated by the following examples. Analyses were performed by capillary gas chromatography using a 30 meter DB-5 column with a flame ionization detector. (35° C. initial temperature, 250° C. injection port temp., initial time=5 minutes, heating rate=20° C./minute, final temp.=240° C.). At these program conditions, EpB had a retention time of 1.3 minutes, acetic acid=1.7 to 1.8 minutes, $Ac_2O$=2.8 minutes., and DAcB=9.4–9.5 minutes. During the early screening runs the integrated peak heights were not corrected for response and are noted as applicable. Runs conducted later in this work were calibrated, again as noted. Batch experiments were carried out in the initial investigations of the esterification process.

BATCH EXPERIMENTS

Example 1

To a 50 mL three-neck flask equipped with condenser, magnetic stirrer, thermocouple, heating mantel and septum sampling port was added 18.0 g (0.176 mol) of $Ac_2O$, 10.3 g (0.147 mol) of EpB, and 2.0 g (0.014 mol, 10 mole % based on EpB) of anhydrous potassium carbonate. The mixture was heated to reflux with magnetic stirring and product formation monitored by periodic sampling. The reflux temperature began at 83° C. and gradually increased. Monitoring of reaction progress via capillary gc (area percentages uncorrected) revealed very selective conversion to DAcB. The mixture remained two-phase but as the temperature increased above 118° C. all of the catalyst dissolved, a clear, orange solution resulted, and the temperature quickly rose to the maximum set-point of 140° C. Total reaction time was approximately 9 hours. Analytical sampling via syringe became impossible at this point, because the liquid solidified before an aliquot could be transferred to a sample vial. A sample of the cooled reaction mixture showed that >95% of the starting EpB had been converted to DAcB (uncorrected for response).

Example 2

The procedure described in Example 1 was repeated using an increased sampling rate. To the 50 mL three-neck flask was added 17.98 g (0.176 mol) of $Ac_2O$, 10.49 g (0.148 mol) of EpB, and 1.99 g (0.014 mol, 10 mole % based on EpB) of anhydrous potassium carbonate. The mixture was heated to reflux with magnetic stirring and product formation monitored by periodic sampling. The reaction temperature increased with conversion over several hours. At a temperature of 116° C., the mixture started to become homogeneous and was clear orange in color at 126° C. Attempts to sample after dissolution started failed because the syringe needle became clogged. The rise from 116° C. to 126° C. occurred over a five-minute period, and the temperature rose another 4° C. to 130° C. over the next five minutes. The temperature was controlled at 130° C. for an additional 20 minutes, then the heat was removed and the reactor temperature rapidly lowered with a cold water bath. GC analysis of the supernatant liquid showed that the reaction had progressed very rapidly between the point that solid catalyst was present and the quench. Total reaction time was 6.5 hours. Conversion increased from approximately 55% to 95% over the 45 minutes between when the last sample could be collected at 111° C. and the point at which the reaction was quenched. It was noted during the quench that reformation of solid occurred almost instantaneously at an indicated temperature of 119° C. The mixture became a slurry at this point but did not seem to get thicker as cooling was continued to room temperature. A summary of reaction times, reaction temperatures and conversions is shown in Table I wherein Reaction Time is the total reaction time (hours) elapsed at the time of each sampling, Reaction Temperature (° C.) is the temperature of the reaction mixture at the time of each sampling, Conversion is $$\frac{\text{Moles } EpB \text{ Converted to } DAcB}{\text{Moles } EpB \text{ Fed to the Reaction Zone}} \times 100$$

and the values given for DAcB are GC area percentages for the amount of DAcB present in the reaction mixture.

TABLE I

| Reaction Time | Reaction Temperature | Conversion | DAcB |
|---|---|---|---|
| 0.0 | — | 0 | 0.00 |
| 0.5 | 87 | 1.3 | 1.90 |
| 1.5 | 88 | 5.1 | 4.41 |
| 2.5 | 89 | 8.0 | 6.84 |
| 3.5 | 92 | 19.5 | 14.05 |
| 4.5 | 96 | 32.6 | 22.40 |
| 5.5 | 106 | 55.2 | 36.04 |
| 5.75 | 111 | 61.9 | 40.14 |
| 6.5 | 130 | 96.6 | 66.06 |

Comparative Example 1

The procedure described in Example 1 was repeated employing 18.05 g (0.176 mol) of $Ac_2O$, 10.27 g (0.147 mol) of EpB, and 1.47 g (0.015 mol, 10 mole % based on EpB) of anhydrous potassium acetate. The mixture was heated to reflux with magnetic stirring and product formation monitored by periodic sampling of the reaction mixture. The reflux temperature began at 83° C. The reaction occurred more slowly than observed for potassium carbonate and had to be shut down and started up over a period of three days for complete reaction to occur. After 19 hours of total reaction time, the temperature had reached 114° C. and the catalyst began to dissolve. Within another hour, total DAcB content jumped from 40.39% to 65.60%, EpB CONVERSION WAS 93.4%, all of the catalyst had dissolved, and the reaction was discontinued. The final color was brown instead of the orange typical of the experiments utilizing potassium carbonate, and slightly more impurities were observed in the chromatogram. A summary of reaction times, reaction temperatures and conversions is shown in Table II wherein Reaction Time, Reaction Temperature (° C.), Conversion and DAcB have the meanings given in the preceding example.

TABLE II

| Reaction Time | Reaction Temperature | Conversion | DAcB |
|---|---|---|---|
| 0.0 | — | 0 | 0.00 |
| 2.0 | 83 | 1.5 | 1.17 |
| 3.0 | 85 | 2.5 | 1.85 |
| 4.5 | 88 | 4.6 | 3.24 |
| 5.5 | 90 | 6.5 | 4.36 |
| 6.5 | 91 | 8.7 | 5.82 |
| 7.5 | 94 | 11.9 | 7.60 |
| 8.5 | 96 | 14.2 | 8.91 |
| 9.5 | 96 | 15.1 | 9.66 |
| 10.5 | 95 | 15.7 | 10.48 |
| 11.5 | 97 | 19.7 | 12.66 |
| 13.0 | 97 | 22.6 | 14.55 |
| 14.0 | 98 | 28.6 | 17.72 |
| 15.5 | 103 | 38.2 | 23.04 |
| 17.5 | 109 | 54.8 | 34.08 |
| 19.0 | 114 | 61.1 | 40.39 |
| 19.5 | 122 | 70.2 | 46.79 |
| 20.0 | 126 | 93.6 | 65.60 |

Example 3

The procedure described in Example 1 was repeated using 18.00 g (0.176 mol) of $Ac_2O$, 10.30 g (0.147 mol) of EpB, and 1.10 g (0.008 mol, 5 mole % based on EpB) of anhydrous potassium carbonate. The mixture was heated as previously described and product formation monitored by periodic sampling. At a temperature of 123° C., the mixture became homogeneous and was clear yellow in color. No problems with sampling were encountered after complete dissolution occurred. About 94% conversion was achieved after six hours of reaction time. A summary of reaction times, reaction temperatures and conversions (uncorrected area percent) is shown in Table III wherein Reaction Time, Reaction Temperature (° C.), Conversion and DAcB have the meanings given in Example 2.

TABLE III

| Reaction Time | Reaction Temperature | Conversion | DAcB |
|---|---|---|---|
| 0.0 | — | 0 | 0 |
| 1.0 | 87 | 2.3 | 2.11 |
| 3.0 | 94 | 10.0 | 3.44 |
| 4.0 | 101 | 35.0 | 23.37 |
| 6.0 | 123 | 94.1 | 64.35 |

Example 3 was repeated with the same quantity of $Ac_2O$ and EpB, but with 0.55 g (0.004 mol, 2.7 mole %) of potassium carbonate. The mixture became clear yellow at 112° C. (9 hours reaction time), and the reaction was discontinued after 10.0 hours and 126° C. A summary of reaction times, reaction temperatures and conversions (uncorrected area percent) is shown in Table IV wherein Reaction Time, Reaction Temperature (° C.), Conversion and DAcB have the meanings given in Example 2

TABLE IV

| Reaction Time | Reaction Temperature | Conversion | DAcB |
|---|---|---|---|
| 0.0 | 85 | 0 | 0.06 |
| 1.0 | 86 | 4.1 | 3.35 |
| 2.0 | 87 | 8.3 | 6.79 |
| 5.0 | 92 | 25.4 | 20.36 |
| 6.5 | 95 | 36.3 | 29.07 |
| 8.0 | 102 | 51.1 | 41.19 |
| 10.0 | 126 | 89.5 | 74.26 |

GC analysis of a sample of the final product showed that it contained 2.80% EpB, 3.52% HOAc, 16.66% $Ac_2O$, 0.03% acetoxybutadiene (c+t), 77.03% DAcB, and 0.20% 1,4-diacetoxy-2-butene (c+t).

Example 4

The procedure described in Example 1 was repeated using 17.98 g (0.176 mol) of $Ac_2O$, 0.33 g (0.147 mol) of EpB, and 1.32 g (0.015 mol, 10 mole % based on EpB) of anhydrous potassium bicarbonate. The mixture was heated to reflux with magnetic stirring and product formation monitored by periodic sampling of the reaction mixture. The analytical method was modified with response factors for EpB, $Ac_2O$, HOAc, and DAcB. $Ac_2O$ was used as the reference peak since it is present throughout all phases of the reaction sequence. Minor peaks were included in the report (uncorrected area percent). All analyses from this point on are corrected for response. As observed in previous run, reflux began at 83° C. The reaction mixture was homogeneous after 4.25 hours of reaction time. The reaction occurred more rapidly than observed for potassium carbonate and appeared to be complete by gc in less than five hours at a final temperature of 123° C. A summary of reaction times, reaction temperatures and compositions of the reaction mixture is shown in Table V wherein Time is the total reaction time (hours) elapsed at the time of each sampling, Temp (° C.) is the temperature of the reaction mixture at the time of each sampling, HOAc is acetic acid, 1,4-DAcB 1,4-diacetoxy-2-butene and Dimer is an ether-linked molecule made up of two DAcB molecules of uncharacterized structure. The values given for EpB, Ac2O, DAcB, HOAc, 1,4-DAcB and Dimer are GC area percentages for each of the components of the reaction mixture at the time of each sampling.

TABLE V

| Time | Temp | EpB | $Ac_2O$ | DAcB | HOAc | 1,4-DAcB | Dimer |
|---|---|---|---|---|---|---|---|
| 0.0 | Ambient | 33.75 | 66.10 | 0.19 | — | — | — |
| 1.0 | 87 | 28.97 | 62.34 | 3.79 | 4.90 | — | 0.03 |
| 2.0 | 91 | 23.16 | 61.43 | 9.18 | 6.22 | 0.03 | 0.06 |
| 3.0 | 96 | 17.89 | 58.13 | 16.78 | 7.20 | 0.05 | 0.09 |
| 4.0 | 108 | 10.74 | 52.53 | 30.01 | 6.73 | 0.08 | 0.13 |
| 4.25 | 115 | 8.09 | 47.53 | 32.90 | 11.47 | 0.10 | 0.14 |
| 4.5 | 123 | 4.69 | 45.22 | 41.15 | 8.74 | 0.11 | 0.15 |
| 4.75 | 122 | 0.92 | 35.26 | 48.46 | 15.36 | 0.15 | 0.16 |

CONTINUOUS OPERATION EXPERIMENTS

The equipment described below was assembled to permit continuous operation of the process: a one-liter, three-neck round-bottom flask equipped with a subsurface feed nozzle, overflow line, reflux condenser, and thermocouple temperature sensor, an EpB/$Ac_2O$ addition tank, a peristaltic pump, and a product receiver. The control scheme took advantage of the effect of feeding enough EpB/$Ac_2O$ to the flask/reaction zone to cause the temperature to drop, primarily because of the boiling point-lowering effect of EpB. When the temperature dropped below the set point, the controller turned off the feed pump. As EpB reacted with $Ac_2O$, the temperature then increased above the set point, and the controller then turned the EpB/$Ac_2O$ feed pump back on to begin another cycle. The thermowell, in addition to accommodating the feed-controlling thermocouple, also contained a second thermocouple connected to another controller that was set at a maximum allowable reactor temperature. This prevented runaway overheating in the event that feed was lost and the reaction temperature continued to climb while the equipment was temporarily unattended.

The product overflow line was electrically traced to prevent crystallization of potassium acetate from plugging the exit line. Reactor level was maintained by manually draining the reactor when the level exceeded a mark on the flask by a centimeter or less. It was found most convenient to make up lost catalyst by manual addition of potassium carbonate (or recycled distillation residue from the flash evaporator) prior to the morning start-up. It was noted that the carbonate granules emitted bubbles during heat-up, possibly due to evolution of $CO_2$ gas as conversion to KOAc occurs. EpB/$Ac_2O$ was added as a mixture to ensure accurate ratios and to eliminate having to keep two pumps simultaneously calibrated. The product was kept under nitrogen and periodically emptied from a 100 mL graduated cylinder receiver.

Example 5

To the one-liter flask/reaction zone of the continuous operation apparatus was added 2.8 g of potassium carbonate (1.5 weight percent of $Ac_2O$/EpB charge), 108 mL (117 g, 1.15 mol) of $Ac_2O$, and 81 mL (70 g, 1.00 mol) of EpB. Heating was started and the DAcB concentration allowed to build as indicated by temperature increases. Samples were periodically withdrawn to monitor the progress of the reaction as shown in Table VI wherein Time, Temp (° C.), EpB, Ac2O, DAcB, HOAc, 1,4-DAcB and Dimer have the meaning given previously and the values given for EpB, Ac2O, DAcB, HOAc, 1,4-DAcB and Dimer are GC area percentages for each of the components of the reaction mixture at the time of each sampling.

TABLE VI

| Time | Temp | EpB | $Ac_2O$ | DAcB | HOAc | 1,4-DAcB | Dimer |
|---|---|---|---|---|---|---|---|
| 1.0 | 89 | 43.38 | 51.51 | 2.27 | 2.84 | — | — |
| 2.0 | 90 | 31.22 | 55.32 | 5.47 | 2.99 | — | 0.11 |
| 4.5 | 92 | 28.52 | 54.32 | 14.32 | 2.83 | — | 0.12 |
| 7.75 | 96 | 23.82 | 44.90 | 25.11 | 6.17 | 0.02 | 0.20 |
| 9.0 | 98 | 24.10 | 44.08 | 29.51 | 2.31 | 0.03 | 0.21 |
| 10.0 | 100 | 26.54 | 39.43 | 31.97 | 2.06 | 0.03 | 0.22 |
| 11.0 | 103 | 20.22 | 38.07 | 39.16 | 2.54 | 0.04 | 0.26 |
| 13.0 | 111 | 20.65 | 29.28 | 47.52 | 2.60 | 0.04 | 0.27 |

After 13 hours of initial operation, feeding of a mixture of $Ac_2O$ and EpB in an $Ac_2O$:EpB mole ratio of 1.15:1.00 was commenced. The feed pump control temperature was set to 115° C. and the maximum reactor temperature heating mantel controller set to 120° C. The $Ac_2O$/EpB feed material was prepared by mixing 216 mL of $Ac_2O$ with 162 mL of EpB. The reactor was heated to reflux and the system allowed to equilibrate. The process was monitored by periodic sampling and analyses. The results are summarized in Table VII wherein Time is the amount of time operated in the continuous mode, the values given for Reactant Feed refer to the amount (mL) of $Ac_2O$/EpB mixture continuously fed to the reaction flask over the period of Time via the subsurface feed nozzle, Product Take-Off is the amount (mL) of crude product removed from the reaction flask during the continuous mode of operation over 6.25 hours of operation, and EpB, HOAc, Ac2O and DAcB have the meanings given above. The total amount of $Ac_2O$/EpB mixture fed during the 6.25 hours of continuous operation was 260 mL–55 mL=205 mL.

TABLE VII

| Time | Reactant Feed | Product Take-Off | EpB | $Ac_2O$ | DAcB | HOAc |
|---|---|---|---|---|---|---|
| 0.0 | 260 | — | 13.45 | 28.35 | 54.74 | 3.45 |
| 4.25 | 115 | 97 | 14.31 | 29.14 | 53.21 | 3.34 |
| 6.25 | 55 | 156 | 13.49 | 28.70 | 54.35 | 3.47 |

The amount of 1,4-DAcB present was 0.06 area percent and the amount of dimer present was 0.27–0.24 area percent. The average production rate was 30 g per hour of crude product containing approximately 16 g of DAcB and the space-time yield was 53 g/L-h DAcB based on a working volume of 300 mL. The production rate slowed slightly as catalyst was removed from reactor and not replaced. The average production rate takes into account faster production at start-up and slower production at shut-down.

Example 6

The continuous operation of Example 5 was resumed with the feed pump control temperature was set to 120° C. and the maximum reactor temperature heating mantel controller set to 125° C. The feed tank was charged with a 1.15:1.00 mole ratio of $Ac_2O$/EpB, 2.5 g of make-up potassium carbonate was added to the contents of the reactor from the previous continuous experiment and the reactor was started up as described in Example 5. The process was monitored by periodic sampling and analyses. The results are summarized in Table VIII wherein Time, Reactant Feed, Product Take-Off and EpB, HOAc, $Ac_2O$ and DAcB have the meanings given above.

TABLE VIII

| Time | Reactant Feed | Product Take-Off | EpB | $Ac_2O$ | DAcB | HOAc |
|---|---|---|---|---|---|---|
| 2.5 | 325 | 90 | 11.40 | 24.74 | 60.17 | 3.69 |
| 5.0 | 230 | 176 | 11.34 | 24.53 | 60.73 | 3.41 |
| 7.5 | 155 | 251 | 11.18 | 24.34 | 60.99 | 3.49 |

The reactor lined out to essentially constant amounts of EpB, $Ac_2O$, DAcB and HOAc at steady state. A total of 325−155=175 mL of $Ac_2O$/EpB mixture was fed during this 7.5 hour experiment. The amount of 1,4-DAcB present was 0.07–0.08 area percent, the amount of dimer present was 0.24–0.22 area percent and the amounts of other unidentified material present ranged from 0.12–0.17 area percent. The average production rate was 40 g per hour of crude product containing approximately 24 g of DAcB and the space-time yield was 81 g/L-h based on a working volume of 300 mL.

Example 7

The continuous operation of Example 5 was resumed with the feed pump control temperature was set to 125° C. and the maximum reactor temperature heating mantel controller set to 130° C. The feed tank was charged with a 1.15:1.00 mole ratio of $Ac_2O$/EpB, 3.9 g of make-up potassium carbonate was added to the contents of the reactor from the continuous experiment and the reactor was started up as described in Example 5. The process was monitored by periodic sampling and analyses. The results are summarized in Table IX wherein Time, Reactant Feed, Product Take-Off and EpB, HOAc, $Ac_2O$ and DAcB have the meanings given above.

TABLE IX

| Time | Reactant Feed | Product Take-Off | EpB | $Ac_2O$ | DAcB | HOAc |
|---|---|---|---|---|---|---|
| 1.5 | 231 | 88 | 9.88 | 21.28 | 65.22 | 3.62 |
| 4.0 | 125 | 196 | 9.38 | 20.79 | 65.81 | 4.02 |
| 7.0 | 35 | 282 | 9.66 | 21.37 | 65.48 | 3.49 |

The amount of 1,4-DAcB present was 0.09 area percent, the amount of dimer present was 0.20–0.17 area percent and the amounts of other unidentified material present ranged from 0.15–0.16 area percent. The average production rate was approximately 45 g per hour of crude product containing approximately 30 g of DAcB and the space-time yield was 100 g/L-h based on a working volume of 300 mL.

The invention has been described in detail with particular reference to preferred embodiments thereof, but it will be understood that variations and modifications can be effected within the spirit and scope of the invention.

I claim:

1. Process for the production of 3,4-diacetoxy-1-butene (DAcB) by the steps of (1) feeding 3,4-epoxy-1-butene (EpB) and acetic anhydride ($Ac_2O$) to a reaction zone while maintaining a concentration of potassium acetate (KOAc) of about 0.5 to 5.0 weight percent, based on the total weight of the materials present in the reaction zone, and (2) removing crude product comprising DAcB from the reaction zone, wherein the KOAc initially is formed in situ by contacting EpB, $Ac_2O$ and a potassium compound selected from potassium carbonate, potassium bicarbonate, potassium hydroxide or a mixture of any two or more thereof and the reaction zone is maintained at a temperature in the range of about 100 to 140° C.

2. Process according to claim 1 wherein the EpB and $Ac_2O$ are fed to the reaction zone in an $Ac_2O$: EpB mole ratio in the range of about 1.1:1 to 2:1 and the potassium compound is selected from potassium carbonate, potassium bicarbonate or a mixture thereof.

3. Process according to claim 1 wherein the EpB and $Ac_2O$ are fed to the reaction zone in an $Ac_2O$: EpB mole ratio in the range of about 1.1:1 to 2:1, the potassium compound is potassium carbonate, and the reaction zone is maintained at a temperature in the range of about 120 to 140° C.

4. Process according to claim 1 wherein the EpB and $Ac_2O$ are fed to the reaction zone in an $Ac_2O$: EpB mole ratio in the range of about 1.1:1 to 2:1, the potassium compound is potassium carbonate, and the concentration of potassium acetate (KOAc) is about 0.5 to 2.0 weight percent.

5. Process for the production of DAcB by the steps of (1) providing a reaction zone containing a reaction mixture comprising EpB, $Ac_2O$, at least about 50 weight percent DAcB and about 0.5 to 5.0 weight percent of dissolved KOAc and having a boiling point of about 100 to 140° C.; (2) feeding EpB and $Ac_2O$ to the reaction mixture of step while maintaining the temperature of the mixture at about 100 to 140° C. and while maintaining a concentration of KOAc of about 0.5 to 5.0 weight percent, based on the total weight of the materials present in the reaction mixture; and (3) removing crude product comprising DAcB from the reaction zone.

6. Process according to claim 5 wherein the reaction mixture of step (1) contains about 50 to 70 weight percent DAcB.

7. Process according to claim 5 wherein the reaction mixture of step (1) contains about 50 to 70 weight percent DAcB and has a boiling point of about 120 to 140° C.; and step (2) is carried out at a temperature of about 120 to 140° C.

8. Process according to claim 5 wherein the reaction mixture contains 0.5 to 2.0 weight percent of dissolved KOAc.

9. Process for the production of DAcB comprising the step of contacting EpB and $Ac_2O$ in the presence of KOAc in a reaction zone to form a product comprising DAcB, EpB, KOAc and $Ac_2O$.

10. Process according to claim 9 wherein the process further comprises the step of removing a portion of the product from the reaction zone and feeding it to a purification zone to recover the DAcB.

* * * * *